US012577183B2

(12) United States Patent
Olayiwola et al.

(10) Patent No.: US 12,577,183 B2
(45) Date of Patent: Mar. 17, 2026

(54) OXYGENATE SEPARATION FOLLOWING OXIDATIVE DEHYDROGENATION OF A LOWER ALKANE

(71) Applicant: NOVA Chemicals (International) S.A., Fribourg (CH)

(72) Inventors: Bolaji Olayiwola, Calgary (CA); Vasily Simanzhenkov, Calgary (CA); Shahin Goodarznia, Calgary (CA); Kamal Serhal, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 753 days.

(21) Appl. No.: 17/953,743

(22) Filed: Sep. 27, 2022

(65) Prior Publication Data

US 2023/0024922 A1     Jan. 26, 2023

Related U.S. Application Data

(63) Continuation of application No. 16/597,156, filed on Oct. 9, 2019, now Pat. No. 11,492,310.

(Continued)

(51) Int. Cl.
*C07C 5/48* (2006.01)
*B01J 19/00* (2006.01)
(Continued)

(52) U.S. Cl.
CPC ............. *C07C 5/48* (2013.01); *B01J 19/0013* (2013.01); *C07C 7/09* (2013.01); *C07C 11/06* (2013.01)

(58) Field of Classification Search
CPC .... B01J 19/00; B01J 19/0006; B01J 19/0013; C07C 5/00; C07C 5/42; C07C 5/48;
(Continued)

(56) References Cited

U.S. PATENT DOCUMENTS

| | | | |
|---|---|---|---|
| 3,728,413 A | 4/1973 | Woerner | |
| 4,464,189 A | 8/1984 | Tedder | |

(Continued)

FOREIGN PATENT DOCUMENTS

| | | |
|---|---|---|
| CA | 2907955 | 11/2014 |
| CA | 2867731 A1 | 4/2016 |

(Continued)

OTHER PUBLICATIONS

BR Office Action in Brazilian Appln. No. 122023020479-4, dated Jul. 9, 2024, 12 pages (with English translation).

(Continued)

*Primary Examiner* — Natasha E Young
(74) *Attorney, Agent, or Firm* — Fish & Richardson P.C.

(57) ABSTRACT

A process, a system, and an apparatus are provided for converting a lower alkane to an alkene. Oxygen and the lower alkane are provided to an ODH reactor to convert at least a portion of the lower alkane to an alkene. An ODH stream comprising the alkene, an oxygenate, steam, and a carbon-based oxide is produced. The bulk of the oxygenate is removed from the ODH outlet stream by non-dilutive cooling, with residual oxygenate being removed using dilutive quenching with a carbonate. Subsequently, separation of the carbon-based oxide from the alkene is achieved using a caustic tower, which also produces spent caustic in the form of a carbonate, which is then used as the carbonate for dilutive quenching. Dilutive quenching using a carbonate allows conversion of the oxygenate to an acetate, which can then be used to simplify separation of the oxygenate from water.

24 Claims, 5 Drawing Sheets

Related U.S. Application Data

(60) Provisional application No. 62/769,205, filed on Nov. 19, 2018.

(51) Int. Cl.
    *C07C 7/09*         (2006.01)
    *C07C 11/06*       (2006.01)

(58) Field of Classification Search
    CPC .. C07C 7/00; C07C 7/005; C07C 7/09; C07C 7/11; C07C 11/00; C07C 11/02; C07C 11/06; C07C 51/00; C07C 51/41; C07C 11/04
    See application file for complete search history.

(56)                References Cited

U.S. PATENT DOCUMENTS

| | | | |
|---|---|---|---|
| 4,899,003 | A | 2/1990 | Manyik et al. |
| 6,166,263 | A | 12/2000 | Etzkorn et al. |
| 7,005,555 | B2 | 2/2006 | Ding et al. |
| 7,319,179 | B2 | 1/2008 | Nieto et al. |
| 7,411,107 | B2 | 8/2008 | Lucy |
| 7,491,843 | B2 | 2/2009 | Jobson et al. |
| 9,993,798 | B2 | 6/2018 | Simanzhenkov et al. |
| 10,427,992 | B2 | 10/2019 | Mitkidis et al. |
| 2004/0267069 | A1 | 12/2004 | Ding et al. |
| 2010/0256432 | A1 | 10/2010 | Arnold et al. |
| 2014/0088331 | A1* | 3/2014 | Rolland ............... B01J 31/0212 585/326 |

| | | | |
|---|---|---|---|
| 2015/0166440 | A1 | 6/2015 | Pavia et al. |
| 2017/0113983 | A1 | 4/2017 | Mitkidis et al. |
| 2019/0315668 | A1 | 10/2019 | Raja et al. |
| 2019/0359546 | A1 | 11/2019 | Mamedov |

FOREIGN PATENT DOCUMENTS

| | | |
|---|---|---|
| EP | 1676901 | 7/2006 |
| JP | S61 5030 A | 1/1986 |
| WO | WO0037399 | 6/2000 |
| WO | WO0044694 | 8/2000 |
| WO | WO2008097785 | 8/2008 |
| WO | WO2015087668 | 6/2015 |
| WO | WO 2017046315 A1 | 3/2017 |
| WO | WO2017072086 | 5/2017 |
| WO | WO 2018148145 A1 | 8/2018 |
| WO | WO2018153831 | 8/2018 |

OTHER PUBLICATIONS

PCT International Search Report and Written Opinion in International Application No. PCT/IB2019/058602, dated Jan. 8, 2020, 9 pages.

PCT International Search Report and Written Opinion in International Application No. PCT/IB2019/058604, dated Jan. 7, 2020, 11 pages.

BR Office Action in Brazilian Appln. No. 112021006830-9, dated Jul. 11, 2023, 7 pages (with English translation).

Communication pursuant to Article 94(3) EPC in EP Appln. No. 19789766.3, mailed on Nov. 21, 2025, 8 pages.

\* cited by examiner

OXYGENATE SEPARATION FOLLOWING OXIDATIVE DEHYDROGENATION OF A LOWER ALKANE

CROSS REFERENCE TO RELATED APPLICATIONS

This application is a continuation application of U.S. patent application Ser. No. 16/597,156, now U.S. Pat. No. 11,492,310, filed on Oct. 9, 2019, which claims the benefit of the filing date of U.S. Provisional Application No. 62/769, 205, filed on Nov. 19, 2018, the contents of both hereby incorporated by reference in their entirety as part of this application.

TECHNICAL FIELD

The present disclosure relates generally to oxidative dehydrogenation (ODH) of a lower alkane into an alkene. In some examples, the present disclosure relates to separation of an ODH product from a process stream.

BACKGROUND

Olefins like ethylene, propylene, and butylene, can be basic building blocks for a variety of commercially valuable polymers. Since naturally occurring sources of olefins may not exist in commercial quantities, polymer producers may rely on methods for converting the more abundant lower alkanes into olefins. Typically, a polymer producer can utilize steam cracking to produce alkenes from the lower alkanes. Steam cracking is a highly endothermic process where steam-diluted lower alkanes are subjected very briefly to a high temperature of at least 800° C. which requires a high energy demand. Additionally, steam cracking can cause coke formation in the reactor which can lead to increased maintenance costs.

Oxidative dehydrogenation (ODH) is an alternative to steam cracking that can be exothermic, can have a low energy demand, and can produce little or no coke. In ODH, a lower alkane is mixed with oxygen in the presence of a catalyst and optionally an inert diluent at low temperatures such as, for example 300° C., to produce the corresponding alkene. In some examples, various other by-products such as, for example, carbon monoxide, carbon dioxide, and an oxygenate may also be produced in the ODH process. The by-products may be subject to further processing prior to being a marketable product or may be disposed of. The additional processing can increase the complexity of a chemical complex and can include a high energy demand.

SUMMARY

In one aspect, a method is provided to convert a lower alkane to an alkene. More specifically, an input stream comprising oxygen and the lower alkane is provided to an oxidative dehydrogenation (ODH) reactor. At least a portion of the lower alkane is converted to the alkene in the ODH reactor and an ODH outlet stream comprising the alkene, an oxygenate, and a carbon-based oxide is produced. The ODH outlet stream is cooled and at least a portion of the oxygenate is condensed. The alkene is separated from the oxygenate to produce an alkene outlet stream and an oxygenate outlet stream. The alkene outlet stream comprises at least a sub-stantial portion of the alkene and at least a substantial portion of the carbon-based oxide. The oxygenate outlet stream comprises at least a substantial portion of the condensed oxygenate.

In another aspect, an apparatus is provided for oxidative dehydrogenation (ODH) of a lower alkane to an alkene. More specifically, the apparatus comprises an ODH reactor, a means for cooling, and a flash drum. The ODH reactor comprises an ODH inlet and an ODH outlet. The ODH inlet is suitable for transporting an ODH inlet stream comprising the lower alkane into the ODH reactor. The ODH outlet is suitable for transporting an ODH outlet stream comprising the alkene, an oxygenate, water in the form of steam, and a carbon-based oxide. The means for cooling is suitable for cooling the ODH outlet stream and condensing at least a portion of the oxygenate. The flash drum comprises a drum inlet, an oxygenate outlet, and an alkene outlet. The drum inlet is in fluid communication with the ODH outlet, to receive the cooled ODH outlet stream. The flash drum is suitable for separating the condensed oxygenate from gas-eous alkene and gaseous carbon-based oxide. The alkene outlet is suitable for transporting an alkene outlet stream comprising at least a substantial portion of the alkene and at least a substantial portion of the carbon-based oxide. The oxygenate outlet is suitable for transporting an oxygenate outlet stream comprising at least a substantial portion of the condensed oxygenate.

In another aspect, a system is provided for oxidative dehydrogenation (ODH) of a lower alkane. More specifi-cally, the system comprises an ODH reactor, a means for cooling, and a flash drum. The ODH reactor is configured to receive an input stream comprising oxygen and the lower alkane. The ODH reactor is configured to produce an ODH outlet stream comprising an alkene, an oxygenate, water in the form of steam, and a carbon-based oxide. The means for cooling is configured to cool the ODH outlet stream to produce a cooled ODH outlet stream. The flash drum is configured to separate the alkene from the oxygenate to produce an alkene outlet stream and an oxygenate outlet stream. The alkene outlet stream comprises at least a sub-stantial portion of the alkene and at least a substantial portion of the carbon-based oxide. The oxygenate outlet stream comprises at least a substantial portion of the con-densed oxygenate.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description of examples taken in conjunction with the accompanying drawings, wherein.

DETAILED DESCRIPTION

Figure 1:
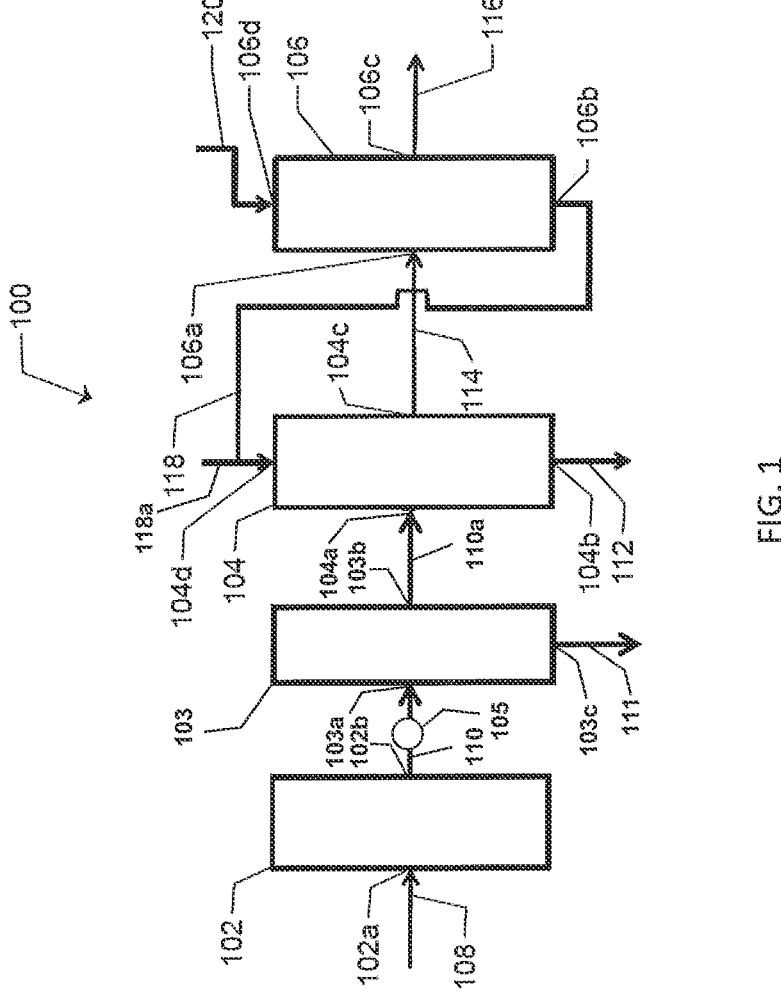
FIG. 1 is a flow diagram illustrating a non-limiting example of a system to convert an alkane to an alkene.

The exemplifications set out herein illustrate certain examples, in one form, and such exemplifications are not to be construed as limiting the scope of the examples in any manner.

Certain exemplary aspects of the present disclosure will now be described to provide an overall understanding of the principles of the structure, function, manufacture, and use of the systems, apparatus, and methods disclosed herein. One or more examples of these aspects are illustrated in the accompanying drawings. Those of ordinary skill in the art will understand that the systems and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

The grammatical articles "a", "an", and "the", as used herein, are intended to include "at least one" or "one or more", unless otherwise indicated, even if "at least one" or "one or more" is expressly used in certain instances. Thus, the foregoing grammatical articles are used herein to refer to one or more than one (i.e., to "at least one") of the particular identified elements. Further, the use of a singular noun includes the plural, and the use of a plural noun includes the singular, unless the context of the usage requires otherwise.

As used herein, the term "substantial portion" means at least 50 percent by weight. A substantial portion can be 50% to 100% by weight such as, for example, at least 60% by weight, at least 70% by weight, at least 80% by weight, at least 90% by weight, or at least 95% by weight.

As used herein, the term "alkane" refers to an acyclic saturated hydrocarbon. In various examples, an alkane consists of hydrogen and carbon atoms arranged in a linear structure in which all of the carbon-carbon bonds are single bonds. An alkane has the general chemical formula $C_nH_{2n+2}$ and in various examples, for a lower alkane, 'n' is in a range of 2 to 4. In various examples, an alkane refers to one or more of ethane, propane, butane, pentane, hexane, octane, decane and dodecane. In various examples, a lower alkane refers to one or more of ethane, propane, and butane.

As used herein, the term "alkene" refers to an unsaturated hydrocarbon that contains at least one carbon-carbon double bond. In various examples, alkene refers to alpha olefins. For example, alkene can refer to one or more of ethylene, propylene, 1-butene, butadiene, pentene, pentadiaene hexene, octene, decene, and dodecene.

As used herein, the terms "alpha olefin" or "α-olefin" refer to a family of organic compounds which are an alkene (also known as olefin) with a chemical formula $C_xH_{2x}$, distinguished by having a double bond at the primary or alpha (α) position. In various examples, alpha olefin refers to one or more of ethylene, propylene, 1-butene, 1-pentene, 1-hexene, 1-octene, 1-decene, and 1-dodecene.

As used herein, the term "fixed bed reactor" refers to one or more reactors, in series or parallel, often including a cylindrical tube filled with catalyst pellets with reactants flowing through the bed and being converted into products. The catalyst in the reactor may have multiple configurations including, for example, one large bed, several horizontal beds, several parallel packed tubes, multiple beds in their own shells, and/or combinations thereof.

As used herein, the term "fluidized bed reactor" refers to one or more reactors, in series or parallel, often including a fluid (e.g., gas or liquid) which can be passed through a solid granular catalyst, which can be shaped as tiny spheres, at a velocity high enough to suspend the solid granular catalyst and cause the solid granular catalyst to behave like a fluid.

As used herein, the term "HDPE" refers to high density polyethylene, which generally has a density of greater or equal to 0.941 g/cm³. HDPE has a low degree of branching. HDPE can be often produced using chromium/silica catalysts, Ziegler-Natta catalysts or metallocene catalysts.

As used herein, the term "LDPE" refers to low density polyethylene, which can be a polyethylene with a high degree of branching with long chains. Often, the density of a LDPE will range from 0.910-0.940 g/cm³. LDPE can be created by free radical polymerization.

As used herein, the term "LLDPE" refers to linear low density polyethylene, which can be a polyethylene that can have significant numbers of short branches resulting from copolymerization of ethylene with at least one α-olefin comonomer. In some examples, LLDPE has a density in the range of 0.915-0.925 g/cm³. In some examples, the LLDPE can be an ethylene hexene copolymer, ethylene octene copolymer, or ethylene butene copolymer. The amount of comonomer incorporated can be from 0.5 mole % to 12 mole % relative to ethylene, in some examples from 1.5 mole % to 10 mole %, and in other examples from 2 mole % to 8 mole %.

As used herein, the term "MDPE" refers to medium density polyethylene, which can be a polyethylene with some short and/or long chain branching and a density in the range of 0.926-0.940 g/cm³. MDPE can be produced using chromium/silica catalysts, Ziegler-Natta catalysts or metallocene catalysts.

As used herein, the term "VLDPE" refers to very low density polyethylene, which can be a polyethylene with high levels of short chain branching with a typical density in the range of 0.880-0.915 g/cc. In some examples, VLDPE can be a substantially linear polymer. VLDPE can be typically produced by copolymerization of ethylene with α-olefins. VLDPE can be produced using metallocene catalysts.

As used herein, the term "gas phase polyethylene process" refers to a process where a mixture of ethylene, optional alpha olefin comonomers, and hydrogen can be passed over a catalyst in a fixed or fluidized bed reactor. The ethylene and optional alpha olefins polymerize to form grains of polyethylene, suspended in the flowing gas, which can pass out of the reactor. In various examples, two or more of the individual reactors are placed in parallel or in series, each of which are under slightly different conditions, so that the properties of different polyethylenes from the reactors are present in the resulting polyethylene blend. In some examples, the catalyst system includes, for example, chromium catalysts, Ziegler-Natta catalysts, zirconocene catalysts, and metallocene catalysts and combinations thereof.

As used herein, the term "high pressure polyethylene process" refers to converting ethylene gas into a white solid by heating it at very high pressures in the presence of minute quantities of oxygen (less than 10 ppm oxygen) at 1000 bar-3000 bar and at 80° C.-300° C. In some examples, the high pressure polyethylene process produces LDPE.

As used herein, the term "low pressure polyethylene process" refers to polymerizing ethylene using a catalyst that in some examples includes aluminum at generally lower pressures than the high pressure polyethylene process. In some examples, the low pressure polyethylene process can be carried out at 10 bar-80 bar and at 70° C.-300° C. In various examples, the low pressure polyethylene process provides HDPE. In various examples, an α-olefin comonomer can be included in the low pressure polyethylene process to provide LLDPE.

As used herein, the term "solution polyethylene process" refers to processes that polymerize ethylene and one or more optional α-olefins in a mixture of lower alkane hydrocarbons in the presence of one or more catalysts. In various examples, two or more of the individual reactors can be placed in parallel or in series, each of which can be under slightly different conditions, so that the properties of different polyethylenes from the reactors are present in the resulting polyethylene blend. In some examples the catalysts include, but are not limited to, chromium catalysts, Ziegler-Natta catalysts, zirconocene catalysts, hafnocene catalysts, phosphinimine catalysts, metallocene catalysts, and combinations thereof.

As used herein, the term "slurry polyethylene process" refers to single-tube loop reactors, double-tube loop reactors or autoclaves (stirred-tank reactors) used to polymerize ethylene and optional α-olefins in the presence of a catalyst system and a diluent. Non-limiting examples of diluents include isobutane, n-hexane, or n-heptane. In some examples, two or more of the individual reactors are placed in parallel or in series, each of which can be under slightly different conditions, so that the properties of different polyethylenes from the reactors are present in the resulting polyethylene blend. In some examples, the catalyst system includes, for example, chromium catalysts, Ziegler-Natta catalysts, zirconocene catalysts, hafnocene catalysts, phosphinimine catalysts, metallocene catalysts, and combinations thereof.

As used herein, the term "long chain branching" refers to a situation where during α-olefin polymerization, a vinyl terminated polymer chain can be incorporated into a growing polymer chain. Long branches often have a length that can be longer than the average critical entanglement distance of a linear (e.g., no long chain branching) polymer chain. In some examples, long chain branching effects melt rheological behavior.

As used herein, the term "short chain branching" refers to a copolymer of ethylene with an α-olefin or with branches of less than 40 carbon atoms. In some examples, the α-olefin or branches are present at less than 20% by weight of the polyethylene, in some examples less than 15% by weight. In some examples, the presence of short chain branches can interfere with the formation of the polyethylene crystal structure and can be observed as a lower density compared with a linear (no short chain branching) polyethylene of the same molecular weight.

As used herein, the term "monomer" refers to small molecules containing at least one double bond that can react in the presence of a free radical polymerization initiator to become chemically bonded to other monomers to form a polymer.

As used herein, the term, "olefinic monomer" includes, without limitation, α-olefins, and in some examples, ethylene, propylene, 1-butene, 1-hexene, 1-octene, and combinations thereof.

As used herein, the term "polyolefin" refers to a material, which is prepared by polymerizing a monomer composition containing at least one olefinic monomer.

As used herein, the term "polyethylene" can include, for example, a homopolymer of ethylene, a copolymer of ethylene, and an α-olefin.

As used herein, the term "polypropylene" can include a homopolymer of propylene such as, for example, isotactic polypropylene and syndiotactic polypropylene, a copolymer of propylene, and an α-olefin.

As used herein, the term "polymer" refers to macromolecules composed of repeating structural units connected by covalent chemical bonds and can include, for example, a homopolymer, a random copolymer, a block copolymer, and a graft copolymer.

As used herein, the term "thermoplastic" refers to a class of polymers that can soften or become liquid when heated and can harden when cooled. In some examples, a thermoplastic can be a high-molecular-weight polymer that can be repeatedly heated and remolded. In various examples, a thermoplastic resin can include a polyolefin and an elastomer that has thermoplastic properties.

As used herein, the terms "thermoplastic elastomers" and "TPE" refer to a class of copolymers or a blend of polymers (in some examples a blend of a thermoplastic and a rubber) which includes materials having both thermoplastic and elastomeric properties.

As used herein, the terms "thermoplastic olefin" or "TPO" refer to polymer/filler blends that contain some fraction of polyethylene, polypropylene, block copolymers of polypropylene, rubber, and a reinforcing filler. The fillers can include, for example, talc, fiberglass, carbon fiber, wollastonite, metal oxy sulfate, and combinations thereof. The rubber can include, for example, ethylene-propylene rubber, EPDM (ethylene-propylene-diene rubber), ethylene-butadiene copolymer, styrene-ethylene-butadiene-styrene block copolymers, styrene-butadiene copolymers, ethylene-vinyl acetate copolymers, ethylene-alkyl (meth)acrylate copolymers, and VLDPE such as those available under the Flexomer® resin trade name from the Dow Chemical Co., Midland, MI, styrene-ethylene-ethylene-propylene-styrene (SEEPS). These can also be used as the materials to be modified by the interpolymer to tailor their rheological properties.

Unless otherwise specified, all molecular weight values are determined using gel permeation chromatography (GPC). Molecular weights are expressed as polyethylene equivalents with a relative standard deviation of 2.9% for the number average molecular weight ("Mn") and 5.0% for the weight average molecular weight ("Mw"). Unless otherwise indicated, the molecular weight values indicated herein are weight average molecular weights (Mw).

Unless otherwise specified, all pressure values are absolute pressure values.

Composition of gaseous streams can be described in many ways, as known to a person skilled in the art. For oxidative dehydrogenation, numerous streams are described and can be partially describe in terms of the chemical composition. Unless otherwise specified, the chemical composition of a chemical species within streams is measured in terms of mole percent (mol %) which is calculated by determining the moles of the species and dividing by the total number of moles of all species in the stream and multiplying by 100. Converting to mass fraction or mass percent is within the knowledge of the person skilled in the art and can be performed given sufficient information about the stream with respect to flow rates, temperature, and pressure.

Oxidative dehydration (ODH) can couple the endothermic dehydration of an alkane with the strongly exothermic oxidation of hydrogen. For example, ODH of an alkane can comprise contacting an alkane and oxygen in an ODH reactor with an ODH catalyst under reaction conditions (e.g., temperature, pressure, flow rate, etc.) that can promote oxidation of the alkane into the corresponding alkene. The corresponding alkene includes hydrocarbons with the same number of carbons as the alkane used in the ODH reactor, but with the addition of one carbon to carbon double bond. For example, utilizing ODH, ethane can be converted to ethylene, propane can be converted to propylene, and butane can be converted to butylene.

Any ODH catalyst known in the art can be suitable for use with the present disclosure. For example, an ODH catalyst containing a mixed metal oxide can be used. Additionally, reaction conditions can be controlled to adjust the selectively and yield of the ODH reactor products. As known in the art, conditions will vary and can be optimized for a particular alkane, for a specific catalyst, a select product, and/or a particular inert diluent.

A product of an ODH reaction can be an oxygenate such as, for example, acetic acid, acrylic acid, maleic acid, and maleic anhydride. The oxygenate can require purification and/or further processing in order to generate a marketable product. For example, water may have to be removed from the oxygenate. Separation of the oxygenate from water can increase the complexity of a quench tower and/or a separation tower due to the small thermal (e.g., boiling point) separation between the oxygenate and the water. In various examples, a mixture of oxygenate and water can be azeotropic. The separation tower may employ a large column, a high quantity of stages, a high reflux ratio, and a high energy demand to separate an azeotropic mixture of oxygenate and water.

Thus, a method, a system, and an apparatus are provided which can enhance the purification of the oxygenate and reduce energy requirements for the purification. More specifically, a method, a system, and an apparatus are provided for converting a lower alkane to an alkene. An input stream comprising oxygen and the lower alkane can be provided to an ODH reactor. At least a portion of the lower alkane can be converted to the alkene in the ODH reactor and an ODH outlet stream comprising the alkene, an oxygenate, water in the form of steam, and a carbon-based oxide can be produced. The ODH outlet stream can then be cooled to promote condensation of at least a substantial portion of the oxygenate and a portion of the steam. The ODH outlet stream can then be subjected to a means for liquid-gas separation to produce a first oxygenate outlet stream comprising at least a substantial portion of the condensed oxygenate and water and an alkene outlet stream comprising at least a substantial portion of the alkene, at least a substantial portion of the carbon-based oxide, and any remaining oxygenate. Using condensation and liquid-gas separation for removing a substantial portion of the oxygenate from the ODH outlet stream is non-dilutive as no additional components are added to the ODH outlet stream.

The alkene outlet stream can be provided to a quench tower and remaining oxygenate can be removed from the alkene outlet stream. The quench tower, as known to a person skilled in the art, includes addition of a quench agent, usually water, and is therefore dilutive as an additional component is added to the stream. A first quench outlet stream comprising at least a substantial portion of the alkene and at least a substantial portion of the carbon-based oxide can be produced in the quench tower. Additionally, a second quench outlet stream comprising at least a substantial portion of the remaining oxygenate can be produced in the quench tower. The first quench outlet stream can be provided to a caustic wash tower. The first quench outlet stream can be contacted with a hydroxide in the caustic wash tower to form a caustic outlet stream comprising a carbonate. The caustic outlet stream can be provided to the quench tower. The alkene outlet stream can be contacted with the caustic outlet stream to form an acetate. The second quench outlet stream can comprise a substantial portion of the acetate.

Referring to FIG. 1, illustrated is a flow diagram of a non-limiting example of a system 100 to convert an alkane to an alkene. As illustrated, an ODH reactor 102, a flash tower 103, a quench tower 104, and a caustic wash tower 106 can be in operative communication. For example, an ODH outlet 102b of the ODH reactor 102 can be in fluid communication with a flash tower inlet 103a of flash tower 103 via an ODH outlet line 110. Additionally, a flash tower outlet 103b of flash tower 103 can be in fluid communication with a quench inlet 104a of the quench tower 104 via alkene outlet line 110a. Additionally, a quench outlet 104c of the quench tower 104 can be in fluid communication with a wash inlet 106a of the caustic wash tower 106 via a quench outlet line 114. Accordingly, the ODH reactor 102 can be in fluid communication with the caustic wash tower 106 via the flash tower 103 and the quench tower 104.

The ODH reactor 102 can comprise an ODH inlet 102*a* which can be configured to receive an ODH inlet stream from an ODH inlet line 108 and can be suitable to transport the ODH inlet stream into the ODH reactor 102. The ODH inlet stream can comprise a gaseous mixture of a lower alkane and oxygen. In various examples, the ODH inlet stream additionally can include at least one of a carbon-based oxide, steam, and an inert diluent. The inert diluent can comprise, for example, nitrogen, carbon dioxide, steam, and methane. In various examples, the carbon-based oxide can comprise at least one of carbon dioxide and carbon monoxide. The concentration of the oxygen and the lower alkane within the mixture in the ODH inlet stream and the temperature and pressure of the ODH inlet stream can be adjusted such that the mixture can be outside of the flammability limits of the mixture.

In various examples, there may be multiple ODH inlet lines configured to provide the ODH inlet stream to the ODH reactor 102. For example, each component (e.g., lower alkane, oxygen, steam, carbon-based oxide, and inert diluent) may be added directly to the ODH reactor 102, each in separate inlet lines (not shown). Alternatively, one or more components may be pre-mixed and added in more than one inlet line. In various example, components may be mixed together prior to the ODH reactor 102 and subsequently introduced into the ODH reactor in a common ODH inlet. In various examples, steam may be added indirectly as water mixed with an additional reactant and the resulting mixture can be preheated before entering the ODH reactor 102. When adding steam indirectly as water, the preheating process can increase the temperature of the mixture so that the water can be substantially converted to steam before entering the ODH reactor 102.

The ODH reactor 102 can include a catalyst capable of catalyzing the ODH of the reactants within the ODH inlet stream to products such as, for example, an alkene, a carbon-based oxide, water, and an oxygenate. The catalyst may be, for example, a mixed metal oxide catalyst.

The catalyst composition, temperature and pressure of the ODH reactor 102, and the composition of the ODH inlet stream can be adjusted in order to vary the composition of products as known by one of ordinary skill in the art. For example, the ratio of the lower alkane to oxygen can be outside of the upper flammability limit of the mixture. In various examples, the oxygen concentration in the ODH inlet stream can be in a range of 0.1% to 30% by weight of the ODH inlet stream, and in some examples range from 0.1% to less than 30% by weight, less than 25% by weight, or less than 20% by weight. In various examples, the lower alkane concentration in the ODH inlet stream can range from 0.1% to 50% by weight of the ODH inlet stream, and in some examples range from 0.1% to less than 50% by weight or less than 40% by weight.

In various examples increasing the steam concentration in the ODH inlet stream can increase the amount of oxygenate produced relative to the alkene produced in the ODH reactor 102. In various examples, reducing the steam concentration in the ODH inlet stream can decrease the amount of oxygenate produced relative to the alkene produced in the ODH reactor 102. The concentration of steam in the ODH inlet stream can be in a range of 0.1% to 40% by weight of the total ODH inlet stream 108, and in some examples range from 0.1% to less than 40% by weight, or less than 25% by weight. In various examples, the concentration of the stream in the ODH inlet stream can be at least 1% by weight. In various examples, the ODH inlet stream can comprise 20% oxygen by weight, 40% lower alkane by weight, and the balance being steam, carbon dioxide, and/or an inert diluent.

In various examples, the ODH process has a selectivity for the corresponding alkene (e.g., ethylene in the case of ethane ODH) of greater than 95% such as, for example, greater than 98%. The gas hourly space velocity (GHSV) within the ODH reactor 102 can be from 500 to 30000 $h^{-1}$ and in some examples the GHSV within the ODH reactor 102 can be greater than 1000 $h^{-1}$. In various examples, the linear velocity within the ODH reactor 102 can be from 10 cm/s to 500 cm/s. In various examples, the weight hourly space velocity (WHSV) within the ODH reactor can be from 2.1 to 25 $h^{-1}$. In various examples, the space-time yield of corresponding alkene (e.g., productivity) in grams(g)/hour per kilogram (kg) of the catalyst can be at least 900 such as, for example, greater than 1500, greater than 3000, or greater than 3500, at an ODH reactor temperature of, for example, 350° C. to 400° C. In various examples, the productivity of the catalyst can increase with increasing temperature in the ODH reactor 102 until the selectivity of the alkene decreases.

Use of an ODH reactor for performing an ODH reaction consistent with the disclosure falls within the knowledge of the person skilled in the art. In various examples, the reaction can be conducted at temperatures in a range of 300° C. to 450° C. such as, for example, 300° C. to 425° C., or 330° C. to 400° C. In various examples, the reaction can be conducted at pressures in a range of 0.5 pounds per square inch (psi) to 100 psi (3.447 to 689.47 kPa) such as, for example, 15 psi to 50 psi (103.4 to 344.73 kPa). In various examples, the lower alkane can have a residence time in the ODH reactor 102 in a range of 0.002 seconds (s) to 30 s, or from 1 s to 10 s.

The products of the ODH reaction can leave the ODH reactor 102 through the ODH outlet 102*b* in an ODH outlet stream. The ODH outlet 102*b* can be configured to receive the ODH outlet stream and can be suitable to transport the ODH outlet stream 110 out of the ODH reactor 102 and into the ODH outlet line 110. In various examples, in addition to the products, the ODH outlet stream can include unreacted components from the ODH inlet stream such as, for example, lower alkane, carbon-based oxide, oxygen, steam, inert diluent, and combinations thereof. In various examples, the temperature of the ODH outlet stream can be in a range of 100° C. to 450° C., such as for example, 300° C. to 425° C., and in certain examples 330° C. to 400° C.

Any of the known reactor types applicable for the ODH of an alkane may be used with the present disclosure. For example, a fixed bed reactor, a fluidized bed reactor, or combinations thereof can be used for the ODH reactor 102. In a typical fixed bed reactor, reactants are introduced into the reactor at an inlet and flow past an immobilized catalyst. Products are formed and leave through the outlet of the reactor. A person skilled in the art would understand which features are required with respect to shape and dimensions of the reactor, inputs for reactants, outputs for products, temperature and pressure control, and means for immobilizing the catalyst.

In a typical fluidized bed reactor, the catalyst bed can be supported by a porous structure or a distributor plate and located near a lower end of the reactor. Reactants flow through the fluidized bed reactor at a velocity sufficient to fluidize the bed (e.g., the catalyst rises and begins to swirl around in a fluidized manner). The reactants can be converted to products upon contact with the fluidized catalyst and the reactants are subsequently removed from an upper end of the reactor. A person of ordinary skill in the art would understand which features are required with respect to shape and dimensions of the reactor, the shape and size of the distributor plate, the input temperature, the output temperature, the reactor temperature and pressure, inputs for reactors, outputs for reactants, and velocities to achieve fluidization.

In various examples, there may be multiple ODH reactors connected in series or in parallel. Each ODH reactor may be the same or different. For example, each ODH reactor can contain the same or different ODH catalyst. In various examples, the multiple ODH reactors can each be a fixed bed reactor, can each be a fluidized bed reactor, or the multiple ODH reactors can be combinations of fixed bed reactors and fluidized bed reactors.

Regardless of the configuration of the ODH reactor 102, the ODH outlet 102b can be in fluid communication with the flash tower inlet 103a of the flash tower 103 via ODH outlet line 110 to direct the ODH outlet stream to the flash tower 103. The ODH outlet stream is subjected to a cooling means 105 prior to reaching flash tower inlet 103a or within flash tower 103. The flash tower outlet 103b can be in fluid communication with the quench inlet 104a of the quench tower 104 via the alkene outlet line 110a to direct the alkene outlet stream to the quench tower 104. The quench inlet 104a can be configured to receive the alkene outlet stream from the alkene outlet line 110a and can be suitable to transport the alkene outlet stream into the quench tower 104.

The cooling means 105 can be any means that cools the ODH outlet stream after it leaves the ODH reactor. This can include using a sufficiently long ODH outlet line 110 that allows the ODH outlet stream to cool to a temperature where the oxygenate begins to condense before reaching flash tower 103. In some embodiments, the most preferable cooling means 105 comprise a heat exchanger, use of which is well known within the art. In some embodiments, the cooling means 105 are an integral part of the flash tower 103. In some examples, the flash tower may be surrounded by a cooling jacket that cools the ODH outlet stream as it enters flash tower 103. In another example, cooling tubes are arranged within the space inside flash tower 103. In some embodiments, a heat exchanger in combination with integrated cooling means are used to cool to ODH outlet stream.

The cooling means can cool the ODH outlet stream to a temperature of less than 200° C. such as, for example, less than 100° C., less than 50° C., less than 40° C., and in some examples, the cooling means 105 can cool the ODH outlet stream to a temperature of 20° C. to 80° C. In various examples, the cooling means 105 can cool the ODH outlet stream to a temperature which induces condensation of the oxygenate such as, for example, to a temperature less than or equal to the boiling point of the oxygenate and/or a temperature that reduces the vapor pressure of the oxygenate. The lower the temperature, without going below a temperature that results in freezing of the water or oxygenate, the greater the degree of condensation, which would be understood by a person skilled in the art.

Flash tower 103 can comprise a flash tower, or any other means that provides for gas-liquid separation. Use of flash towers is well known. At least a substantial portion of the oxygenate and water, in the form of steam, within the ODH outlet stream may be in a liquid state after being subjected to cooling means 105 and may exit flash tower 103 through a first oxygenate outlet 103c, as a first oxygenate outlet stream, and into the first oxygenate outlet line 111. In various examples, the first oxygenate outlet stream can comprise at least 0.5 mol % oxygenate, such as, for example, at least 2.0 mol % oxygenate, at least 5 mol %, or 0.5 mol % to 15 mol % oxygenate. The first oxygenate outlet stream can additionally comprise water of from 80 mol % to 99.5 mol %.

A portion of the oxygenate and water within the ODH outlet stream, including liquid and gaseous forms, may leave the flash tower 103 as part of the alkane outlet stream. These portions are referred to as remaining oxygenate and remaining water, respectively.

In various examples, the alkene outlet stream may be subject to a second cooling means prior to or as an integral part of quench tower 104. The second cooling means can be configured to adjust the temperature of the alkene outlet stream, for example, by cooling to a temperature of less than 200° C. such as, for example, less than 100° C., less than 50° C., less than 40° C., and in some examples, the second cooling means can cool the alkene outlet stream to a temperature of 20° C. to 80° C. In various examples, the second cooling means can cool the alkene outlet stream to a temperature which induces condensation of the remaining oxygenate such as, for example, a temperature less than or equal to the boiling point of the remaining oxygenate and/or a temperature that reduces the vapor pressure of the remaining oxygenate. The second cooling means can use any means known in the art. For example, the second cooling means can be a standalone heat exchanger separate from a quench tower. In various examples, the second cooling means can be an integrated heat exchanger that is part of a quench tower. In further examples, the second cooling means may include a combination of standalone heat exchanger and an integrated heat exchanger.

The quench tower 104 can comprise a quench tower, an oxygenate scrubber, the like, or combinations thereof. The quench tower 104 can be configured to quench the components in the alkene outlet stream and remove at least a substantial portion of the alkene from the alkene outlet stream. In various examples, the quench tower 104 can facilitate the removal of remaining oxygenate and water from the alkene outlet stream. The quench tower 104 can produce a first quench outlet stream comprising at least a substantial portion of the alkene and at least a substantial portion of the carbon-based oxide from the alkene outlet stream. In various examples, the first quench outlet stream can comprise additional components from the alkene outlet stream such as, for example, a portion of the oxygen, a portion of the oxygenate, a portion of the inert diluent, a portion of the steam, and a portion of the unreacted alkane. The first quench outlet stream exits the quench tower 104 through the quench outlet 104c. The quench outlet 104c can be configured to receive the first quench outlet stream and can be suitable to transport the first quench outlet stream out of the quench tower 104 into the quench outlet line 114.

The quench tower 104 can produce a second quench outlet stream comprising at least a substantial portion of any remaining oxygenate present in the alkene outlet stream and in some examples, an acetate as discussed herein. In various examples, the second quench outlet stream can comprise additional components from the alkene outlet stream such as, for example, a substantial portion of the remaining water (e.g., steam), as well as lower alkane, alkene, oxygen, and carbon-based oxide. The second quench outlet stream can exit the quench tower 104 through second quench outlet 104b of the quench tower 104. The second quench outlet 104b can be configured to receive the second quench outlet stream and can be suitable to transport the second quench outlet stream out of the quench tower 104 into the second quench outlet line 112.

The quench tower 104 also comprises a carbonate inlet 104*d* for providing a quenching agent such as water via quench agent line 118*a*, or a carbonate solution via return line 118. Use of quench towers is well known. A person skilled in the art would understand that quenching condenses and dilutes the oxygenate. The result is that second quench outlet stream comprises a lower mol % of the oxygenate compared to the first oxygenate outlet stream. When using a carbonate solution as the quench agent the effect is more pronounced as a portion of the oxygenate is converted to an acetate, as will be described.

In some examples, the quench agent is provided to the quench tower at a temperature of less than 200° C. such as, for example, less than 100° C., less than 50° C., less than 40° C., and in some examples, the quench agent is provided to the quench tower at a temperature of 20° C. to 80° C. In various examples, the quench agent can be provided to the quench to a temperature which induces condensation of the remaining oxygenate such as, for example, a temperature less than or equal to the boiling point of the remaining oxygenate and/or a temperature that reduces the vapor pressure of the remaining oxygenate.

The quench outlet 104*c* can be in fluid communication with the wash inlet 106*a* of the caustic wash tower 106 via the quench outlet line 114 to direct the first quench outlet stream to the caustic wash tower 106. The wash inlet 106*a* can be configured to receive the first quench outlet stream from the quench outlet line 114 and can be suitable to transport the first quench outlet stream into the caustic wash tower 106.

The caustic wash tower 106 can comprise the wash inlet 106*a*, a wash outlet 106*c*, a caustic inlet 106*d*, and a caustic outlet 106*b*. The caustic inlet 106*d* can be configured to receive a hydroxide stream comprising a hydroxide from a hydroxide line 120 and can be suitable to transport the hydroxide stream into the caustic wash tower 106. The hydroxide may be, for example, an aqueous solution of at least one of sodium hydroxide, potassium hydroxide, and ammonia hydroxide. In various examples, the aqueous solution comprises at least 0.5 mol % hydroxide, such as, for example, at least 1.0 mol % hydroxide, at least 1.25 mol %, or 0.5 mol % to 1.75 mol % hydroxide.

The caustic wash tower 106 can be configured to contact the hydroxide stream with the first quench outlet stream. In various examples, where the carbon-based oxide comprises carbon dioxide, the hydroxide can react with carbon dioxide in the first quench outlet stream to form a carbonate. The reaction can remove at least a substantial portion of the carbon-based oxide (e.g., carbon dioxide) from the first quench outlet stream and produce a wash outlet stream and a caustic outlet stream. The carbonate may be, for example, at least one of sodium bicarbonate, potassium carbonate, and ammonium bicarbonate. For example, the reaction of sodium hydroxide and carbon dioxide is shown in Scheme 1.

$$CO_2 + NaOH \leftrightarrow NaHCO_3 \qquad \text{Scheme 1}$$

The wash outlet stream can comprise unreacted components from the first quench outlet stream. The wash outlet 106*c* can be configured to receive the wash outlet stream and can be suitable to transport the wash outlet stream out of the caustic wash tower 106 into the wash outlet line 116.

The caustic outlet stream can comprise a substantial portion of the carbonate and in some examples, at least one of water, hydroxide, and oxygenate. The caustic outlet 106*b* can be configured to receive the caustic outlet stream and can be suitable to transport the caustic outlet stream into the return line 118. The return line 118 can be configured to receive the caustic outlet stream and output the caustic outlet stream into a carbonate inlet 104*d* of the quench tower 104.

In various examples, the caustic outlet stream can comprise at least 0.5 mol % carbonate, such as, for example, at least 2.0 mol % carbonate, at least 5 mol %, or 0.5 mol % to 15 mol % carbonate. The caustic outlet stream can additionally comprise water of from 80 mol % to 99.5 mol %.

The quench tower 104 can be configured to contact the caustic outlet stream with the alkene outlet stream. In various examples, the quench tower 104 can be configured to react the caustic outlet stream with the alkene outlet stream to form an acetate. In various examples, the quench tower 104 can react the carbonate with the oxygenate, and in some examples, with water and hydroxide, to form the acetate. The acetate can comprise at least one of sodium acetate, potassium acetate, and ammonium acetate. As an example, the reaction of sodium bicarbonate and the oxygenate to form sodium acetate is illustrated by the reaction in Scheme 2.

$$NaHCO_3 + CH_3COOH \leftrightarrow CO_2 + H_2O + NaC_2H_3O_2 \qquad \text{Scheme 2}$$

In various examples, the mole ratio of the carbonate in the caustic outlet stream to oxygenate in the alkene outlet stream can be in a range of 0.8:1 to 1.2:1 such as for example, 1:1. In various examples, the mole ratio of the carbonate in the caustic outlet stream to oxygenate in the alkene outlet stream can be greater than 1:1 such as, for example, 2:1.

In various examples, the quench tower 104 can be configured to maintain a pH in a range of 2 to 12 such as, for example, 4 to 7. In various examples, the quench tower 104 can be configured to maintain a pH in a range of a pKa of the oxygenate to a pKa of the carbonate in order to facilitate the formation of the acetate. In various example, the oxygenate comprises acetic acid having a pKa of 4.7 and sodium bicarbonate having a pKa of 6.4.

The first quench outlet stream can comprise a substantial portion of the carbon-based oxide produced in the quench tower 104 and from the alkene outlet stream. The second quench outlet stream can comprise the oxygenate, the acetate, and water. Adding the caustic outlet stream to the quench tower can decrease the amount of oxygenate and increase the amount of acetate in the first quench outlet stream. The decrease in oxygenate in the first quench outlet stream can be a result of the conversion of the oxygenate to the acetate. The conversion of the oxygenate to the acetate can facilitate the removal of the oxygenate from the alkene outlet stream and limit the oxygenate from exiting the quench tower 104 in the first quench outlet stream.

In various examples, the second quench outlet stream can comprise at least 0.1 mol % oxygenate, such as, for example, at least 0.5 mol % oxygenate, at least 1 mol %, or 0.1 mol % to 5 mol % oxygenate. The second quench outlet stream can additionally comprise at least 0.25 mol % acetate, such as, for example, at least 1.75 mol % oxygenate, at least 5 mol %, or 0.25 mol % to 15 mol % acetate water of from 80 mol % to 99.5 mol %.

Figure 2:
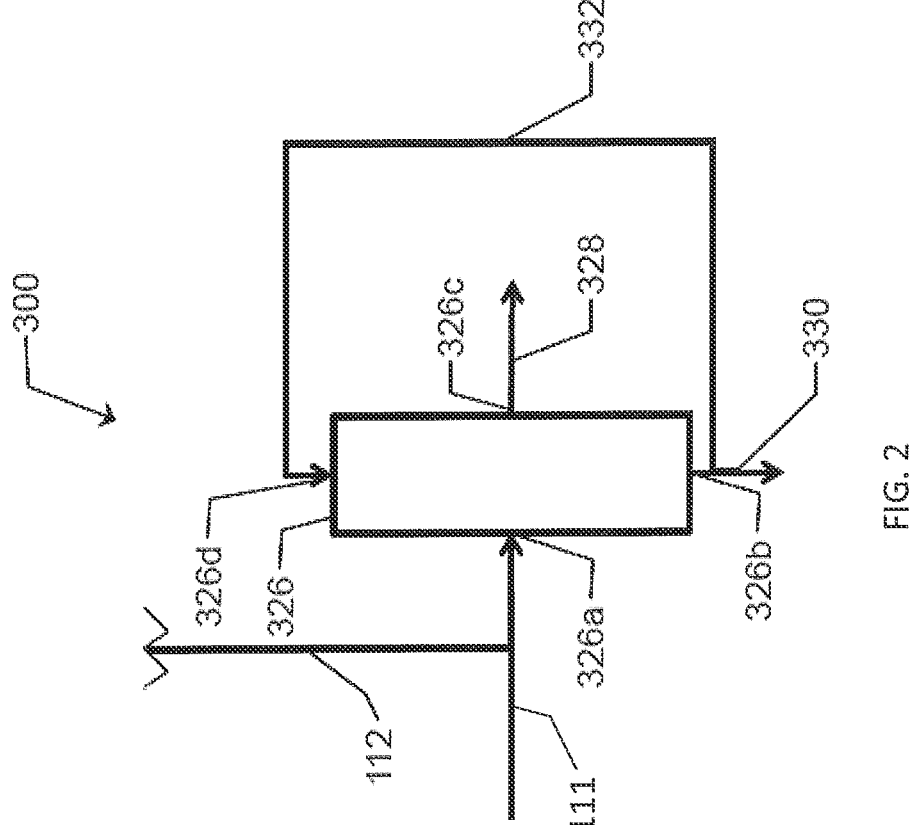
FIG. 2 is a flow diagram illustrating a non-limiting example of a system comprising a separation tower.

In various examples, the oxygenate in the first oxygenate outlet stream and the second quench outlet stream may be subject to further processing. For example, referring to FIG. 2, the oxygenate can be separated from the acetate in a separation tower 326. FIG. 2 is a flow diagram of a non-limiting example of a system 300 comprising the separation tower 326. As illustrated, the separation tower 326 has a separation inlet 326*a*, a first separation outlet 326*b*, and a second separation outlet 326*c*. The separation inlet 326*a* can be configured to receive the first oxygenate outlet stream from first oxygenate outlet line 111 and the second quench outlet stream from the second quench outline line 112 and may be suitable to transport at least one of the first oxygenate outlet stream and the second quench outlet stream into the separation tower 326.

The separation tower 326 can separate the oxygenate from the acetate and, in various examples, the separation tower 326 can separate the oxygenate from water. The presence of the acetate in the separation tower 326 can enhance the separation of oxygenate from the water. For example, the acetate and oxygenate may disassociate and/or react with water to form an acetate ion (e.g., $CH_3COO^-$) and an acid (e.g., $H_3O^+$, $Na^+$). Since the acetate and oxygenate can form a common ion, an increase in the concentration of one of the acetate and oxygenate can affect the other. For example, the reactions of sodium acetate ($C_2H_3NaO_2$), acetic acid ($CH_3COOH$), bicarbonate ion ($HCO_3^-$), carbon dioxide ($CO_2$), and water ($H_2O$) is illustrated in Scheme 3.

$$CH_3COOH+H_2O \leftrightarrow CH_3COO^- +H_3O^+$$

$$H_2O+HCO_3 \leftrightarrow CO_3^{2-} +H_3O^+$$

$$2H_2O+CO_2 \leftrightarrow HCO_3^- +H_3O^+$$

$$C_2H_3NaO_2 \leftrightarrow (\text{or} \rightarrow)CH_3COO^- +Na^+ \qquad \text{Scheme 3}$$

As illustrated in Scheme 3, sodium acetate can form an acetate ion which can affect the equilibrium reaction of acetic acid and water. For example, the sodium acetate can cause the equilibrium reaction of acetic acid and water to have a higher preference for the separate species of acetic acid and water than an acetate ion and an acid relative to without the presence of acetate.

The separation tower 326 can comprise various equipment known to those of ordinary skill in the art. For example, the separation tower 326 can comprise an extraction tower, a packed column, a sieve-tray column, a spray column, a KARR column, a rotating disc contactor, a stirred cell extractor, a rectification tower, a stripper, and combinations thereof. In various examples, the separation tower 326 can comprise a liquid-liquid extractor. Accordingly, the acetate in the oxygenate inlet stream can increase the efficiency of the separation tower 326 and can facilitate efficient separation of the oxygenate from water.

The separation tower 326 can produce a second separation outlet stream comprising a substantial portion of the oxygenate from at least one of the first oxygenate outlet stream and the second quench outlet stream. In various examples, the second separation outlet stream can comprise additional components from at least one of the first oxygenate outlet stream and the second quench outlet stream, such as, for example, water. In various examples, the second separation outlet stream can comprise at least 80 mol % oxygenate such as, for example, at least 90 mol % oxygenate, at least 95 mol % oxygenate, or 80 mol % to 100 mol % oxygenate by weight. The second separation outlet stream can exit the separation tower 326 through the second separation outlet 326c of the separation tower 326. The second separation outlet 326c can be configured to receive the second separation outlet stream and can be suitable to transport the second separation outlet stream out of the separation tower 326 into the second separation outlet line 328.

The separation tower 326 can produce a first separation outlet stream comprising a substantial portion of the acetate from the second quench outlet stream and in various examples, a substantial portion of the water from the second quench outlet stream. In various examples, the first separation outlet stream can comprise at least 10% acetate by weight such as, for example, at least 30% acetate by weight, at least 50% acetate by weight, or 30% to 70% acetate by weight. In various examples, the first separation outlet stream can comprise at least 5% water by weight such as, for example, at least 10% water by weight, at least 25% water by weight, or 15% to 50% water by weight. The first separation outlet stream can exit the separation tower 326 through the first separation outlet 326b of the separation tower 326. The first separation outlet 326b can be configured to receive the first separation outlet stream and can be suitable to transport the first separation outlet stream out of the separation tower 326 into the first separation outlet line 330.

The separation tower 326 can be configured with a recycle line 332 in fluid communication with the first separation outlet line 330 and/or first separation outlet 326b. The recycle line 332 can be configured to recycle a portion of the acetate from the first separation outlet stream to the separation tower 326 via the recycle inlet 326d. The recycle line 332 can be configured to receive a portion of the first separation outlet stream and can be suitable to transport a recycle stream to a recycle inlet 326d of the separation tower 326. The recycle inlet 326d can be configured to receive the recycle stream and can be suitable to transport the recycle stream into the separation tower 326. For example, the recycle stream can comprise a portion of the acetate from the first separation outlet stream, and in various examples, a portion of the water from the first separation outlet stream.

The recycle line 332 can be configured to recycle the acetate from the first separation tower outlet stream until a select concentration of acetate is achieved in the separation tower 326. In various examples and referring to FIGS. 1 and 3, the return line 118 can enable additional generation of acetate in the quench tower 104 which would flow to the separation tower 326 through the second quench outlet line 112 to increase the concentration of acetate in the separation tower 316.

In various examples, a supplemental acetate stream can be added to the separation tower 326. In various examples, the supplemental acetate can comprise ethyl acetate.

Figure 3:
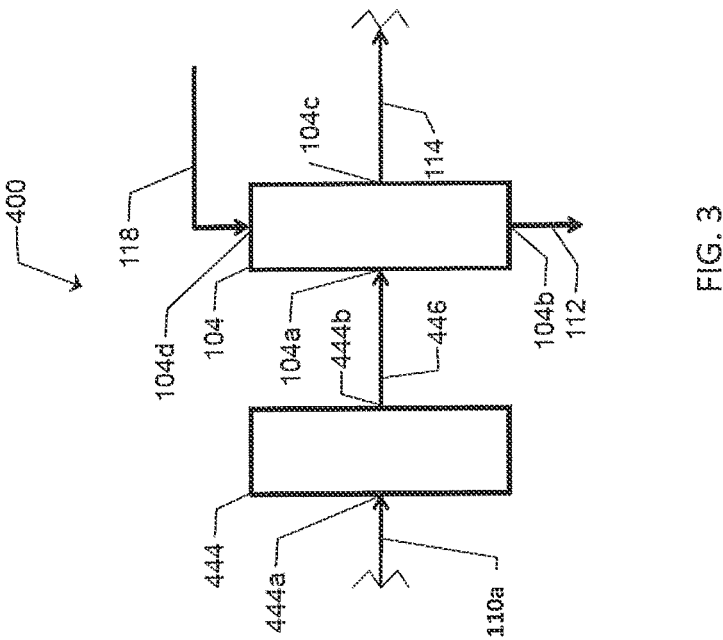
FIG. 3 is a flow diagram illustrating a non-limiting example of a system comprising an oxygen remover.

In various examples, an oxygen remover 444 can be disposed at any point intermediate the ODH reactor 102 and the caustic wash tower 106. FIG. 3 is a flow diagram of a non-limiting embodiment of a system 400 comprising an oxygen remover 444 when situated intermediate the flash tower 103 and the quench tower 104. As illustrated, the oxygen remover 444, comprising a remover inlet 444a and a remover outlet 444b, can be provided in fluid communication with the flash tower 103 (FIG. 1) via alkene outlet line 110a and the quench tower 104 via remover outlet line 446. The remover inlet 444a can be configured to receive the alkene outlet stream and can be suitable to transport the alkene outlet stream into the oxygen remover 444. The oxygen remover 444 can remove a substantial portion of the oxygen in the alkene outlet stream and produce a remover outlet stream comprising the alkene outlet stream with the substantial portion of the oxygen removed. The oxygen remover 444 can be of various designs as known in the art. The remover outlet 444b can be configured to receive the remover outlet stream and can be suitable to transport the remover outlet stream out of the oxygen remover 444 into the remover outlet line 446. The quench inlet 104a of the quench tower 104 can be configured to receive the remover outlet stream.

In another embodiment, the oxygen remover 444 can be situated downstream the ODH reactor 102 and upstream the flash tower 103. In another embodiment, the oxygen remover 444 can be situated down stream the quench tower 104 and upstream the caustic tower 106. The oxygen remover precedes the caustic wash tower 106, or an amine tower (described below), as residual oxygen within the first quench outlet stream may affect operability of the caustic wash tower, or amine tower. Minimizing the level of oxygen within the first alkene outlet stream may also be achieved by altering ODH reaction conditions, as would be apparent to a person skilled in the art.

Figure 4:
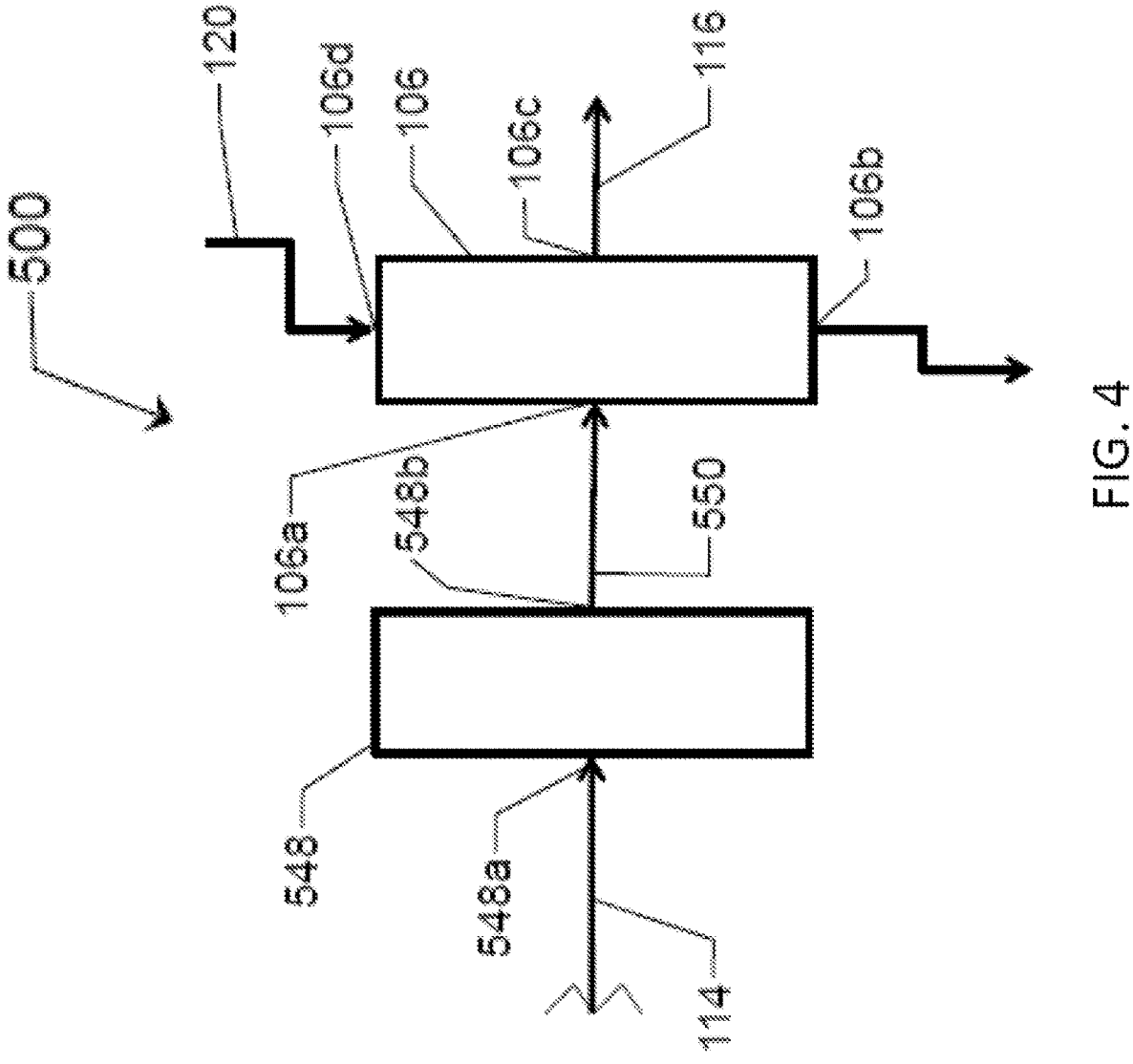
FIG. 4 is a flow diagram illustrating a non-limiting example of a system comprising an amine tower.

Referring to FIG. 4, in various examples, an amine tower 548 can be disposed intermediate the quench tower 104 and the caustic wash tower 106. FIG. 4 is a flow diagram of a non-limiting example of a system 500 comprising an amine tower 548. As illustrated, the amine tower 548, comprising an amine tower inlet 548a and an amine tower outlet 548b, can be provided in fluid communication with the quench tower 104 (FIG. 1) via quench outlet line 114 and the caustic wash tower 106 via amine tower outlet line 550. The amine tower inlet 548a can be configured to receive the first quench outlet stream and can be suitable to transport the first quench outlet stream into the amine tower 548. The amine tower 548 can remove a substantial portion of carbon dioxide in the quench outlet stream and produce an amine tower outlet stream comprising the first quench outlet stream with the substantial portion of the carbon dioxide removed. The amine tower 548 can be of various designs as known in the art.

The amine tower outlet 548b can be configured to receive the amine tower outlet stream and can be suitable to transport the amine tower outlet stream out of the amine tower 548 into the amine tower outlet line 550. The wash inlet 106a of the caustic wash tower 106 can be configured to receive the amine tower outlet stream from the amine tower outlet line 550.

Having a high efficiency oxygenate removal prior to the amine tower 548 can limit, and in some examples prevent, amine degradation to presence of the oxygenate in the amine tower 548. For example, the oxygenate can form heat stable salts with amine in the amine tower 548 which can degrade the efficiency and shorten the operational life of the amine tower 548.

Figure 5:
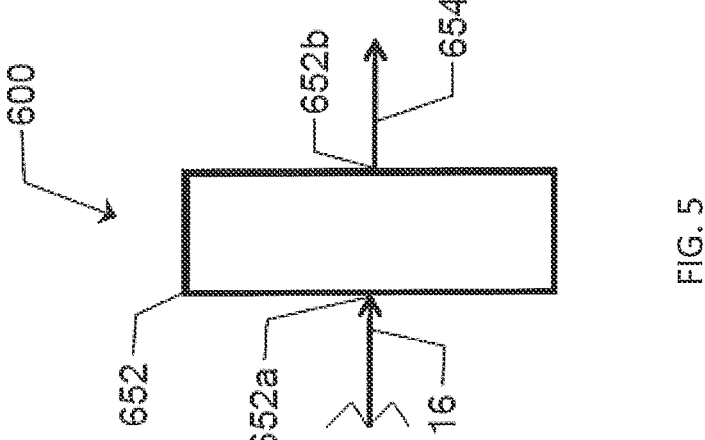
FIG. 5 is a flow diagram illustrating a non-limiting example of a system comprising a polymerization reactor.

Referring to FIG. 5, in various examples, a polymerization reactor 652 can be in fluid communication with the caustic wash tower 106 via the wash outlet line 116. FIG. 5 is a flow diagram of a non-limiting example of a system 600 comprising a polymerization reactor 652. As illustrated, the polymerization reactor 652, comprising a polymerization inlet 652a and a polymerization outlet 652b, can be provided in fluid communication with the caustic wash tower 106 via the wash outlet line 116. The polymerization inlet 652a can be configured to receive the ODH outlet stream and can be suitable to transport the ODH outlet stream into the polymerization reactor 652. The polymerization reactor 652 can produce a polymer from the alkene and produce a polymerization outlet stream comprising the polymer. In various examples, the polymer comprises at least one of polyethylene, polypropylene, and polybutlyene. The polymerization reactor 652 can be of various designs as known in the art. The polymerization outlet 652b can be configured to receive the polymerization outlet stream and can be suitable to transport the polymerization outlet stream out of the polymerization reactor 652 into the polymerization outlet line 654.

Concentrations of the components within the system can be measured any at point in the process using any means known in the art. For example, a detector such as a gas chromatograph, an infrared spectrometer, and a Raman spectrometer can be disposed downstream or upstream of ODH reactor 102, quench tower 104, caustic wash tower 106, separator 238, separation tower 326, oxygen remover 444, amine tower 548, and polymerization reactor 652.

In various examples, the ODH inlet stream 108 can comprise mixtures that fall within the flammability limits of the components. For example, the mixture may exist in conditions that prevent propagation of an explosive event. In these examples, the flammable mixture can be created within a medium where ignition can be immediately quenched. In various examples, oxygen and the lower alkanes can be mixed at a point where they are surrounded by a flame arresting material. Thus, any ignition can be quenched by the surrounding material. Flame arresting material includes, for example, metallic or ceramic components, such as stainless steel walls or ceramic supports. In various examples, oxygen and lower alkanes can be mixed at a low temperature, where an ignition event may not lead to an explosion, then the mixture can be introduced into the ODH reactor before increasing the temperature. Therefore, the flammable conditions may not exist until the mixture can be surrounded by the flame arresting material inside of the reactor.

In various examples, the olefins produced using an ODH reactor, or any of the processes or complexes described herein, can be used to make various olefin derivatives utilizing a polymerization reactor. Olefin derivatives include, but are not limited to, polyethylene, polypropylene, ethylene oxide, propylene oxide, polyethylene oxide, polypropylene oxide, vinyl acetate, vinyl chloride, acrylic esters (e.g., methyl methacrylate), thermoplastic elastomers, thermoplastic olefins, blends thereof, and combinations thereof. In various examples, ethylene and optionally α-olefins can be produced in an ODH reactor, or any of the processes or complexes described herein, and are used to make polyethylene utilizing a polymerization reactor. The polyethylene made from the ethylene and optional α-olefins described herein can include homopolymers of ethylene, copolymers of ethylene and α-olefins, resulting in HDPE, MDPE, LDPE, LLDPE and VLDPE.

The polyethylene produced using the ethylene and optional α-olefins described herein can be produced using any suitable polymerization process and equipment. Suitable ethylene polymerization processes include, but are not limited to gas phase polyethylene processes, high pressure polyethylene processes, low pressure polyethylene processes, solution polyethylene processes, slurry polyethylene processes and suitable combinations of the above arranged either in parallel or in series.

A process for converting a lower alkane to an alkene according to the present disclosure can include providing an input stream comprising oxygen and the lower alkane to an ODH reactor 102. In various examples, providing the input stream to an ODH includes providing oxygen and the lower alkane via separate streams. At least a portion of the lower alkane can be converted to the alkene in the ODH reactor 102. In various examples, the alkane can comprise ethane and the alkene comprises ethylene. In various examples, the alkane can comprise propane and the alkene comprises propylene. In various examples, the alkane comprises butane and the alkene can comprise butylene. An ODH outlet stream comprising the alkene, water in the form of steam, an oxygenate, and a carbon-based oxide may be produced. In various examples, the ODH outlet stream can comprise at least one of an unreacted alkane and oxygen.

The ODH outlet stream is cooled to allow condensation of a portion of the oxygenate and a portion of the steam. The cooled ODH outlet stream is provided to a flash tower 103, or other means for gas-liquid separation, and at least a substantial portion of the condensed oxygenate and at least a substantial portion of the condensed steam are removed from the ODH outlet stream to produce an alkene outlet stream comprising at least a substantial portion of the alkene and at least a substantial portion of the carbon-based oxide and a first oxygenate outlet stream comprising at least a substantial portion of the condensed oxygenate and at least a substantial portion of the condensed steam. In various examples, the alkene outlet stream can comprise at least one of oxygenate, steam, unreacted alkane, and oxygen. Oxygenate and steam present in the alkene outlet stream, referred to as remaining oxygenate and remaining steam, comprise the portions of the oxygenate and steam within the ODH outlet stream that fail to condense during cooling, or are carried by the gaseous alkene and gaseous carbon-based oxide as the alkene outlet stream exits the flash tower 103.

The alkene outlet stream can be provided to a quench tower 104 and the remaining oxygenate and the remaining steam can be removed from the alkene outlet stream in the quench tower 104 to produce a first quench outlet stream comprising at least a substantial portion of the alkene and at least a substantial portion of the carbon-based oxide. Additionally, the quench tower 104 can produce a second quench outlet stream comprising at least a substantial portion of the remaining oxygenate and at least a portion of the remaining steam. Quench towers typically involve the quenching of a gaseous stream with water, or other quench agent, to promote condensation of components within the gaseous stream. The condensed components along with the quench agent fall to the bottom of the tower where they can be removed. The gaseous components rise and can be removed from a location near the top end of the quench tower. The temperature of the quench agent is ideally below that of the condensation point of the component that is targeted for removal. For oxygenates, such as acetic acid, the temperature of the quench agent is, for example, between 20° C. and 100° C.

In various examples, at least one of the ODH outlet stream and the alkene outlet stream can be provided to an oxygen remover 444 prior to the quench tower 104. Oxygen can be removed from at least one of the ODH outlet stream and the alkene outlet stream in the oxygen remover 444 and to reduce the levels of oxygen within at least one of the ODH outlet stream and the alkene outlet stream to from 0 to 5 parts per million (ppm)

The first quench outlet stream can be provided to a caustic wash tower 106. The quench outlet stream can be contacted with a hydroxide to form a caustic outlet stream comprising a carbonate. In various examples, the first quench outlet stream is contacted with the hydroxide in the caustic wash tower 106.

In various examples, the first quench outlet stream can be provided to an amine wash tower 548 prior to the caustic waste tower 106. A substantial portion of the carbon-based oxide can be removed from the first quench outlet stream. The first quench outlet stream with the substantial portion of the carbon-based oxide removed can be provided to the caustic waste tower 106. Use of amines such as diethanolamine, monoethanolamine, methyldiethanolamine, is well known for treating gases to remove carbon-based oxides.

The caustic outlet stream can be provided the quench tower 104 where it acts as a quench agent, and the alkene outlet stream can be contacted with the caustic outlet stream to form an acetate. In various examples, the alkene outlet stream is contacted with the caustic outlet stream in the quench tower 104. The second quench outlet stream outlet stream can comprise a substantial portion of the acetate. In various examples, the pH of the quench tower 104 can be maintained in a range of 2 to 12 such as, for example 4 to 7. In various examples, the pH of the quench tower 104 can be maintained in a range of a pKa of the oxygenate to a pKa of the carbonate.

In various examples, the second quench outlet stream can be provided to a separation tower 326. The oxygenate can be separated from the acetate within the second quench outlet stream. A second oxygenate outlet stream comprising a substantial portion of the oxygenate from the second quench outlet stream can be produced. An extraction outlet stream comprising a substantial portion of the acetate from the oxygenate stream can be produced. In various examples, a portion of the acetate from the extraction outlet stream can be recycled to the separation tower 326. In various examples, a supplemental acetate can be provided to the separation tower 326 such as, for example, ethyl acetate. In various examples, the first oxygenate outlet stream can be provided to the separation tower 326.

In various examples, olefin derivatives can be produced from the alkene.

The present disclosure can provide an alternative use for the caustic waste stream which limits, and in some examples, can eliminate a need to dispose of the caustic waste stream. Additionally, the reuse of the caustic waste stream can provide a useful product of acetate which can aid in oxygenate separation from the quench outlet stream and purification of oxygenate in the separation tower. The efficient removal of the oxygenate from the quench outlet stream can length the operational light of downstream equipment such as protecting the amine tower against fouling and amine solution degradation. Moreover, the acetate can be sold. Furthermore, the efficient purification of the oxygenate can create a marketable product such as, for example, glacial acetic acid.

EXAMPLES

Computational modeling of a liquid-liquid separation vessel using equations from Scheme 3 using ASPEN Plus® version 8.6 chemical process simulation software, commercially available from Aspen Technology, Inc. Bedford, Massachusetts, was used to demonstrate the effect of altering the composition of the feed, as mass fraction, to the separation tower, the feed representing the second quench outlet stream, on the composition of the second oxygenate outlet stream and the composition of the extraction outlet stream. The feed components chosen are typical for an ODH process of ethane, and include water and acetic acid, with trace amounts (not shown) of ethane, ethylene, carbon dioxide. Use of acetate in the quench tower results in sodium acetate contributing to the feed composition.

Example 1

Example 1 represents a feed composition that corresponds to a second quench outlet stream where the ODH outlet stream was not cooled or subjected to non-dilutive separation prior to quenching in the presence of sodium acetate. The feed was modeled at a total mass flow rate of 6980 kg/hr and at a pressure of 185.7 kPa gauge.

Example 2

Example 2 represents a feed composition that corresponds to a second quench outlet stream where the ODH outlet stream was not cooled or subjected to non-dilutive separation prior to quenching in the presence of sodium acetate. The feed was modeled at a total mass flow rate of 55891 kg/hr and at a pressure of 465 kPa gauge.

Example 3

Example 3 represents a feed composition that corresponds to a second quench outlet stream where the ODH outlet stream was cooled and subjected to non-dilutive separation prior to quenching in the presence of sodium acetate. The feed was modeled at a total mass flow rate of 11259 kg/hr and at a pressure of 450 kPa gauge.

Example 4

Example 4 represents a feed composition that corresponds to a second quench outlet stream where the ODH outlet stream was cooled and subjected to non-dilutive separation prior to quenching in the presence of sodium acetate. The feed was modeled at a total mass flow rate of 9259 kg/hr and at a pressure of 450 kPa gauge.

TABLE 1

| | | Feed | | | | Extraction Outlet Stream | | | | Second oxygenate outlet stream | | | |
|---|---|---|---|---|---|---|---|---|---|---|---|---|---|
| | | | | | | | Example | | | | | | |
| | | 1 | 2 | 3 | 4 | 1 | 2 | 3 | 4 | 1 | 2 | 3 | 4 |
| Mass | $CH_3OOH$ | 0.219 | 0.024 | 0.144 | 0.175 | 0.013 | 0.000 | 0.070 | 0.016 | 0.942 | 0.954 | 0.855 | 0.923 |
| | $Na^+$ | 0.153 | 0.228 | 0.145 | 0.176 | 0.196 | 0.240 | 0.160 | 0.213 | 0.000 | 0.000 | 0.000 | 0.000 |
| | $CH_3COOH^-$ | 0.392 | 0.586 | 0.372 | 0.453 | 0.504 | 0.616 | 0.411 | 0.548 | 0.000 | 0.000 | 0.001 | 0.000 |
| | $H_2O$ | 0.235 | 0.162 | 0.338 | 0.196 | 0.235 | 0.144 | 0.359 | 0.222 | 0.052 | 0.046 | 0.144 | 0.366 |

As shown in Table 1, the separation tower, as aided by the sodium acetate, produced the second oxygenate outlet stream comprising at least 85% by weight of acetic acid. The separation tower produced an extraction outlet stream comprising at least 99% of the sodium acetate. The sodium acetate can be recycled into the separation tower and/or can be a commercially marketable product. Additionally, the acetic acid in the second separation outlet can be a commercially marketable product.

The feed streams in the examples take into account the effect of cooling prior to the quench tower. One skilled in the art would recognize that when the ODH outlet stream is not cooled prior to quenching that a larger quantity of water would be required to quench the steam and acetic acid present in the ODH outlet stream. This explains why in example 2 a feed composition lower in acetic acid than examples 3 and 4 was chosen, despite the fact that in examples 3 and 4 a substantial portion of the acetic acid was removed prior to the quench tower. A smaller quantity of water was required for quenching in examples 3 and 4 resulting in a higher mass fraction for those samples.

The examples demonstrate that acetic acid produced in an ODH process can be isolated in a more concentrated from using non-dilutive separation, and that the remainder can be captured as a more dilute solution. The dilute solution can be treated to increase the concentration to a marketable level, and this treatment is simplified by adding spent caustic in the form of a carbonate to the quenching step.

Embodiments

1. A method for converting a lower alkane to an alkene comprising:
    providing oxygen and the lower alkane to an oxidative dehydrogenation (ODH) reactor;
    converting at least a portion of the lower alkane to the alkene in the ODH reactor and producing an ODH outlet stream comprising the alkene, an oxygenate, and a carbon-based oxide;
    cooling the ODH outlet stream and condensing at least a portion of the oxygenate;
    separating the alkene and the carbon-based oxide from condensed oxygenate to produce an alkene outlet stream comprising at least a substantial portion of the alkene and at least a substantial portion of the carbon-based oxide and a first oxygenate outlet stream comprising at least a substantial portion of condensed oxygenate.
2. The method of embodiment 1 wherein the ODH outlet stream comprises from 0.1 mol % to 20 mol % of the oxygenate
3. The method of embodiment 1 or 2 wherein the ODH outlet stream is cooled using a heat exchanger.
4. The method of embodiment 1 or 2 wherein the ODH outlet stream is cooled to a temperature below the boiling point of the oxygenate.
5. The method of any of embodiments 1 to 3 wherein the oxygenate is acetic acid and the ODH outlet stream is cooled to a temperature from 20° C. to 120° C.
6. The method of any of embodiments 1 to 5 wherein separating the alkene from the condensed oxygenate is achieved using a flash drum.
7. The method of any of embodiments 1 to 6 wherein the oxygenate in the first oxygenate outlet stream comprises from 0.5 mol % to 15 mol %.
8. The method of embodiment 1, further comprising:
    providing the alkene outlet stream to a quench tower;
    removing at least a portion of remaining oxygenate from the alkene outlet stream in the quench tower to produce a first quench outlet stream comprising at least a substantial portion of the alkene from the alkene outlet stream and at least a substantial portion of the carbon-based oxide from the alkene outlet stream, and a second quench outlet stream comprising at least a substantial portion of the remaining oxygenate.
9. The method of embodiment 8, further comprising:
    providing the first quench outlet stream to a caustic wash tower;

contacting the first quench outlet stream with a hydroxide in the caustic wash tower to form a caustic outlet stream comprising a carbonate;

providing the caustic outlet stream to the quench tower; and contacting the alkene outlet stream with the caustic outlet stream to form an acetate, wherein the second quench outlet stream comprises a substantial portion of the acetate.

10. The method of embodiment 9, wherein the carbonate comprises at least one of sodium bicarbonate, potassium carbonate, or ammonium bicarbonate.

11. The method of embodiment 9, wherein the hydroxide comprises at least one of sodium hydroxide, potassium hydroxide, or ammonium hydroxide.

12. The method of embodiment 9, wherein the acetate comprises at least one of sodium acetate, potassium acetate, or ammonium acetate.

13. The method of embodiment 9, wherein the carbon-based oxide comprises carbon dioxide and further comprising providing the first quench outlet stream to an amine wash tower and removing a substantial portion of the carbon dioxide from the first quench outlet stream prior to providing the first quench outlet stream to the caustic wash tower.

14. The method of embodiment 9, further comprising maintaining a pH of the quench tower in a range of a pKa of the oxygenate to a pKa of the carbonate.

15. The method of embodiment 9, further comprising maintaining a pH of the quench tower in a range of 2 to 12.

16. The method of embodiment 9 further comprising:

providing the second quench outlet stream to an extraction tower; and separating the oxygenate from the acetate within the second quench outlet stream to produce a second oxygenate outlet stream comprising a substantial portion of the oxygenate from the second quench outlet stream and an extraction outlet stream comprising a substantial portion of the acetate from the second quench outlet stream.

17. The method of embodiment 16, further comprising recycling a portion of the acetate from the extraction outlet stream to the extraction tower.

18. The method of any of embodiments 16 and 17 further comprising providing the first oxygenate outlet stream comprising a substantial portion of the oxygenate from the ODH outlet stream to the extraction tower 19. The method of embodiment 18 wherein the oxygenate in the second oxygenate outlet stream comprises from 80 mol % to 98 mol %.

20. The method of any of embodiments 1 to 19, wherein the ODH outlet stream further comprises at least one of water, an unreacted alkane, or oxygen.

21. The method of embodiment 20, further comprising providing the ODH outlet stream to an oxygen remover and removing oxygen from the ODH outlet stream in the oxygen remover.

22. The method of any of the preceding embodiments, wherein the carbon-based oxide comprises at least one of carbon monoxide or carbon dioxide.

23. The method of any of the preceding embodiments, wherein the oxygenate comprises at least one of acetic acid, acrylic acid, maleic acid, or maleic anhydride.

24. The method of any of the preceding embodiments, wherein the lower alkane comprises ethane and the alkene comprises ethylene.

25. The method of any of embodiments 1 through 23, wherein the lower alkane comprises propane and the alkene comprises propylene.

26. The method of any of the preceding embodiments, wherein the alkene is used to make an olefin derivative.

27. The method of embodiment 26, wherein the olefin derivative comprises at least one of a polyethylene, a polypropylene, an ethylene oxide, a propylene oxide, a polyethylene oxide, a polypropylene oxide, a thermoplastic elastomer, or a thermoplastic olefin.

28. The method of embodiment 27, wherein the olefin derivative comprises a polyethylene selected from at least one of a homopolymer of ethylene, a copolymer of ethylene and an α-olefin, a high density polyethylene (HDPE), a medium density polyethylene (MDPE), a low density polyethylene (LDPE), a linear low density polyethylene (LLDPE), and a very low density polyethylene (VLDPE).

29. An apparatus for oxidative dehydrogenation (ODH) of a lower alkane to an alkene, the apparatus comprising:

an ODH reactor comprising an ODH inlet and an ODH outlet, the ODH inlet suitable for transporting an ODH inlet stream comprising oxygen and the lower alkane into the ODH reactor, the ODH outlet suitable for transporting an ODH outlet stream comprising the alkene, steam, an oxygenate, and a carbon-based oxide out of the ODH reactor;

a heat exchanger comprising a heat exchanger inlet and a heat exchanger outlet, the heat exchange inlet in fluid communication with the ODH outlet to receive the ODH outlet stream, the heat exchanger suitable for cooling the ODH outlet stream and promoting condensation of at least a portion of the oxygenate and at least a portion of the steam, and the heat exchanger outlet suitable for transporting the cooled ODH outlet stream; and a flash drum comprising a drum inlet, an oxygenate outlet, and an alkene outlet, the drum inlet in fluid communication with the heat exchanger outlet to receive the cooled ODH outlet stream, the flash drum suitable for promoting separation of at least a substantial portion of the condensed oxygenate and at least a substantial portion of the condensed steam from the alkene and the carbon-based oxide, the alkene outlet suitable for transporting an alkene outlet stream comprising at least a substantial portion of the alkene and at least a substantial portion of the carbon-based oxide, the oxygenate outlet suitable for transporting a first oxygenate outlet stream comprising at least a substantial portion of the condensed oxygenate and a substantial portion of the condensed steam.

30. The apparatus of embodiment 29, further comprising:

a quench tower comprising a quench inlet, a carbonate inlet, a first quench outlet, and a second quench outlet, the quench inlet in fluid communication with the alkene outlet to receive the alkene outlet stream, the first quench outlet suitable for transporting a first quench outlet stream comprising at least a substantial portion of the alkene from the alkene outlet stream, the second quench outlet suitable for transporting a second quench outlet stream comprising at least a substantial portion of remaining oxygenate from the alkene outlet stream.

31. The apparatus of embodiment 29, further comprising:

a caustic wash tower comprising a wash inlet, a wash outlet, a caustic inlet, and a caustic outlet, the wash inlet in fluid communication with the first quench outlet to receive the first quench outlet stream, the caustic outlet suitable for transporting a caustic outlet stream comprising a carbonate; and a return line in fluid communication with the caustic outlet to receive the caustic outlet stream and output the caustic outlet stream into the carbonate inlet of the quench tower.

32. The apparatus of embodiment 31, wherein the carbonate comprises at least one of sodium bicarbonate, potassium carbonate, or ammonium bicarbonate.

33. The apparatus of embodiment 31, wherein the caustic inlet is suitable for transporting at least one of sodium hydroxide, potassium hydroxide, or ammonium hydroxide to the caustic wash tower.

34. The apparatus of embodiment 31, wherein the acetate comprises at least one of sodium acetate, potassium acetate, or ammonium acetate.

35. The apparatus of embodiment 31, wherein the carbon-based oxide comprises carbon dioxide and further comprising an amine wash tower comprising an amine inlet and an amine outlet, the amine inlet in fluid communication with the first quench outlet to receive the first quench outlet stream, the amine wash tower suitable to remove at least a substantial portion of the carbon dioxide from the first quench outlet stream, and the amine outlet in fluid communication with the wash inlet of the caustic wash tower to output the first quench outlet stream into the wash inlet.

36. The apparatus of embodiment 31, wherein the quench tower is suitable for a pH in a range of a pKa of the oxygenate to a pKa of the carbonate.

37. The apparatus of embodiment 31, wherein the quench tower is suitable for a pH in a range of 2 to 12.

38. The apparatus of embodiment 31, further comprising:

an extraction tower comprising an extraction inlet, a first extraction outlet, and a second extraction outlet, the extraction inlet in fluid communication with the second quench outlet to receive the second quench outlet stream, the first extraction outlet suitable for transporting a first extraction outlet stream comprising a substantial portion of the oxygenate from the second quench outlet stream, the second extraction outlet suitable for transporting a second extraction outlet stream comprising at least a substantial portion of the acetate.

39. The apparatus of embodiment 38, wherein the extraction tower further comprises a recycle line in fluid communication with the second extraction outlet to receive the second extraction outlet stream and output at least a portion of the second extraction outlet stream into the extraction inlet of the extraction tower.

40. The apparatus of embodiment 29, wherein the ODH outlet stream further comprises at least one of water, an unreacted alkane, or oxygen.

41. The apparatus of any of embodiments 29 through 40, further comprising an oxygen remover comprising a remover inlet and a remover outlet, the oxygen remover suitable to remove oxygen from at least one of the ODH outlet stream, the alkene outlet stream and the first quench outlet stream.

42. The apparatus of any of embodiments 29 through 41, wherein the carbon-based oxide comprises at least one of carbon monoxide or carbon dioxide.

43. The apparatus of any of embodiments 29 through 42, wherein the oxygenate comprises at least one of acetic acid, acrylic acid, maleic acid, or maleic anhydride.

44. The apparatus of any of embodiments 29 through 43, wherein the lower alkane comprises ethane and the alkene comprises ethylene.

45. The apparatus of any of embodiments 29 through 43, wherein the lower alkane comprises propane and the alkene comprises propylene.

46. The apparatus of any of embodiments 29 through 45, further comprising a polymerization reactor suitable to make an olefin derivative.

47. The apparatus of embodiment 46, wherein the olefin derivative comprises at least one of a polyethylene, a polypropylene, an ethylene oxide, a propylene oxide, a polyethylene oxide, a polypropylene oxide, a thermoplastic elastomer, or a thermoplastic olefin.

48. The apparatus of embodiment 47, wherein the olefin derivative comprises a polyethylene selected from at least one of a homopolymer of ethylene, a copolymer of ethylene and an $\alpha$-olefin, a high density polyethylene (HDPE), a medium density polyethylene (MDPE), a low density polyethylene (LDPE), a linear low density polyethylene (LLDPE), and a very low density polyethylene (VLDPE).

49. A system for oxidative dehydrogenation (ODH) of a lower alkane to an alkene, the system comprising:

an ODH reactor configured to receive an input stream comprising oxygen and the lower alkane, the ODH reactor configured to produce an ODH outlet stream comprising an alkene, an oxygenate, steam, and a carbon-based oxide;

a means for cooling configured to cool the ODH outlet stream and condense at least a portion of the oxygenate and a portion of the steam and to produce a cooled ODH outlet stream; and a flash tower configured to separate the alkene from the oxygenate to produce an alkene outlet stream comprising at least a substantial portion of the alkene and at least a substantial portion of the carbon-based oxide and a first oxygenate outlet stream comprising at least a substantial portion of condensed oxygenate and at least a substantial portion of condensed steam.

50. The system of embodiment 49, further comprising:

a quench tower configured to receive the alkene outlet stream and remove at least a portion of remaining oxygenate from the alkene outlet stream in the quench tower to produce a first quench outlet stream comprising at least a substantial portion of the alkene from the alkene outlet stream and at least a substantial portion of the carbon-based oxide from the alkene outlet stream, and a second quench outlet stream comprising at least a substantial portion of the remaining oxygenate.

51. The system of embodiment 50, further comprising:

a caustic wash tower configured to receive the first quench outlet stream and configured to contact the first quench outlet stream with a hydroxide in the caustic waste tower to form a caustic outlet stream comprising a carbonate; and a return line in fluid configured to receive the caustic outlet stream and output the caustic outlet stream into the quench tower;

the quench tower configured to contact the alkene outlet stream with the caustic outlet stream to form an acetate, wherein the second quench outlet stream comprises a substantial portion of the acetate.

52. The system of embodiment 51, wherein the carbonate comprises at least one of sodium bicarbonate, potassium carbonate, or ammonium bicarbonate.

53. The system of embodiment 51, wherein the hydroxide comprises at least one of a sodium hydroxide, potassium hydroxide, or ammonium hydroxide.

54. The system of embodiment 51, wherein the acetate comprises at least one of sodium acetate, potassium acetate, or ammonium acetate.

55. The system of embodiment 51, wherein the carbon-based oxide comprises carbon dioxide and further comprising an amine wash tower configured to receive the first quench outlet stream and remove at least a substantial portion of the carbon dioxide from the first quench outlet stream prior to providing the first quench outlet stream to the caustic wash tower.

56. The system of any of embodiments 50 through 55, wherein the quench tower is configured to maintain a pH in a range of a pKa of the oxygenate to a pKa of the carbonate.

57. The system of any of embodiments 50 through 55, wherein the quench tower is configured to maintain a pH in a range of 2 to 12.

58. The system of any of embodiments 51 through 57, further comprising:
   an extraction tower configured to receive the second quench outlet stream and separate the oxygenate from the acetate within the second quench outlet stream to produce a second oxygenate outlet stream comprising a substantial portion of the oxygenate from the second quench outlet stream and an extraction outlet stream comprising a substantial portion of the acetate from the second quench outlet stream.

59. The system of embodiment 58, where the extraction tower is configured to receive the first oxygenate outlet stream.

60. The system of embodiments 58 or 59, wherein the extraction tower further comprises a recycle line configured to receive the second extraction outlet stream and output at least a portion of the second extraction outlet stream into the extraction tower.

61. The system of any of embodiments 49 through 60, wherein the ODH outlet stream further comprises at least one of water, an unreacted alkane, or oxygen.

62. The system of any of embodiments 50 through 61, further comprising an oxygen remover configured to receive and remove oxygen from at least one of the ODH outlet stream, the alkene outlet stream, and the first quench outlet stream.

63. The system of any of embodiments 49 through 62, wherein the carbon-based oxide comprises at least one of carbon monoxide or carbon dioxide.

64. The system of any of embodiments 49 through 63, wherein the oxygenate comprises at least one of acetic acid, acrylic acid, maleic acid, or maleic anhydride.

65. The system of any of embodiments 49 through 64, wherein the lower alkane comprises ethane and the alkene comprises ethylene.

66. The system of any of embodiments 49 through 64, wherein the lower alkane comprises propane and the alkene comprises propylene.

One skilled in the art will recognize that the herein described components, devices, operations/actions, and objects, and the discussion accompanying them are used as examples for the sake of conceptual clarity and that various configuration modifications are contemplated. Consequently, as used herein, the specific examples/embodiments set forth and the accompanying discussion are intended to be representative of their more general classes. In general, use of any specific exemplar is intended to be representative of its class, and the non-inclusion of specific components, devices, operations/actions, and objects should not be taken limiting.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. A system comprising:
   an oxidative dehydrogenation (ODH) reactor to convert a lower alkane to an alkene and discharge an ODH outlet stream comprising the alkene, an oxygenate, and a carbon-based oxide;
   a heat exchanger to cool the ODH outlet stream to condense oxygenate in the ODH outlet stream;
   a flash tower to receive the ODH outlet stream as cooled from the heat exchanger and discharge an alkene outlet stream comprising the alkene and the carbon-based oxide and discharge a first oxygenate outlet stream comprising oxygenate as condensed and water;
   a quench tower to contact the alkene outlet stream with a quenching agent comprising water and carbonate to remove oxygenate from the alkene and discharge a first quench outlet stream comprising the alkene and carbon-based oxide and a second quench outlet stream comprising acetate, water, and oxygenate;
   an extraction tower to receive the first oxygenate outlet stream and the second quench outlet stream to separate oxygenate from acetate and water and discharge an extraction outlet stream comprising acetate and water; and
   a recycle line to recycle to the extraction tower a portion of the extraction outlet stream as discharged.

2. The system of claim 1, wherein the recycle line is configured to recycle directly the portion of the extraction outlet stream to the extraction tower.

3. The system of claim 1, wherein the recycle line is coupled to an inlet of the extraction tower and coupled to an outlet line from the extraction tower conveying the extraction outlet stream as discharged from the extraction tower.

4. The system of claim 1, wherein the quench tower is configured to form acetate from the carbonate and the oxygenate, wherein forming the acetate reduces an amount of the oxygenate in the first quench outlet stream, wherein the oxygenate comprises acetic acid, and wherein a mole ratio of the carbonate in the quenching agent to the oxygenate in the alkene outlet stream is at least 0.8.

5. The system of claim 1, wherein the carbonate comprises at least one of sodium bicarbonate, potassium carbonate, or ammonium bicarbonate, and wherein the acetate comprises at least one of sodium acetate, potassium acetate, or ammonium acetate.

6. The system of claim 1, comprising a caustic wash tower to contact the first quench outlet stream with a hydroxide to discharge a caustic outlet stream comprising carbonate to the quench tower for the quenching agent.

7. The system of claim 6, wherein the hydroxide comprises at least one of sodium hydroxide, potassium hydroxide, or ammonium hydroxide.

8. The system of claim 1, wherein concentration of the oxygenate in the first oxygenate outlet stream is in a range of 0.5 mol % to 15 mol %, wherein the flash tower comprises a flash drum, and wherein the extraction tower comprises a liquid-liquid extractor.

9. The system of claim 1, wherein the first oxygenate outlet stream comprises water in a range of 80 mol % to 99.5 mol %.

10. A system comprising:

an oxidative dehydrogenation (ODH) reactor to convert a lower alkane to an alkene in presence of oxygen and discharge an ODH outlet stream comprising the alkene, an oxygenate, and a carbon-based oxide;

a heat exchanger to cool the ODH outlet stream to condense oxygenate in the ODH outlet stream;

a flash tower to receive the ODH outlet stream as cooled from the heat exchanger and discharge an alkene outlet stream comprising the alkene and the carbon-based oxide and discharge a first oxygenate outlet stream comprising oxygenate as condensed and water;

a quench tower to contact the alkene outlet stream with a quenching agent comprising water and carbonate to remove remaining oxygenate from the alkene and discharge a first quench outlet stream comprising the alkene and carbon-based oxide and a second quench outlet stream comprising acetate, water, and remaining oxygenate;

an extraction tower to receive the first oxygenate outlet stream and the second quench outlet stream to separate oxygenate from acetate and water and discharge a first extraction outlet stream comprising oxygenate and a second extraction outlet stream comprising acetate and water; and a recycle line to recycle to the extraction tower a portion of the extraction outlet stream as discharged.

11. The system of claim 10, wherein the recycle line is configured to directly recycle the portion of the extraction outlet stream to the extraction tower.

12. The system of claim 10, wherein the lower alkane comprises ethane and the alkene comprises ethylene, or wherein the lower alkane comprises propane and the alkene comprises propylene, or a combination thereof.

13. The system of claim 10, wherein the ODH outlet stream further comprises at least one of water, an unreacted alkane, or oxygen.

14. The system of claim 10, wherein the extraction tower is configured to enhance separation of the oxygenate from the water in the extraction tower via presence of the acetate increasing an equilibrium of the oxygenate and water as separate species, and wherein the oxygenate comprises acetic acid.

15. The system of claim 10, wherein a mole ratio of the carbonate in the quenching agent to the oxygenate in the alkene outlet stream is in a range of 0.8 to 1.2.

16. A system comprising:

an oxidative dehydrogenation (ODH) reactor to receive oxygen and an alkane, convert the lower alkane to an alkene, and discharge an ODH outlet stream comprising the alkene, an oxygenate, and a carbon-based oxide;

a heat exchanger to cool the ODH outlet stream to condense oxygenate in the ODH outlet stream;

a flash tower to receive the ODH outlet stream as cooled from the heat exchanger and discharge an alkene outlet stream comprising the alkene and the carbon-based oxide and discharge a first oxygenate outlet stream comprising oxygenate as condensed and water;

a quench tower to contact the alkene outlet stream with a quenching agent comprising water and carbonate to separate remaining oxygenate from the alkene and convert remaining oxygenate by contact with carbonate into acetate and discharge a first quench outlet stream comprising the alkene and carbon-based oxide and a second quench outlet stream comprising acetate, water, and remaining oxygenate;

an extraction tower to receive the first oxygenate outlet stream and the second quench outlet stream to separate oxygenate from acetate and water and discharge a first separation outlet stream as a second oxygenate outlet stream comprising oxygenate and a second separation outlet stream as an extraction outlet stream comprising acetate and water; and a recycle line to recycle directly to the extraction tower a portion of the extraction outlet stream as discharged.

17. The system of claim 16, wherein the carbon-based oxide comprises at least one of carbon monoxide or carbon dioxide, and wherein the oxygenate comprises at least one of acetic acid, acrylic acid, maleic acid, or maleic anhydride.

18. The system of claim 16, wherein the alkane comprises ethane and the alkene comprises ethylene, and wherein the acetate facilitates separation of the oxygenate from water in the extraction tower.

19. The system of claim 16, wherein concentration of oxygenate in the first oxygenate outlet stream is less than 15 mol %.

20. The system of claim 16, wherein the extraction tower comprises a liquid-liquid extractor that separates oxygenate from acetate and water via liquid-liquid extraction.

21. The system of claim 16, wherein the second quench outlet stream comprises a substantial portion of the acetate formed in the quench tower.

22. The system of claim 16, wherein the second oxygenate outlet stream comprises a substantial portion of the oxygenate from the second quench outlet stream, wherein the extraction outlet stream comprises a substantial portion of the acetate from the second quench outlet stream, and wherein presence of the acetate in the extraction tower increases efficiency of separation in the extraction tower.

23. The system of claim 16, wherein the oxygenate in the second oxygenate outlet stream comprises from 80 mol % to 98 mol %.

24. The system of claim 16, wherein the oxygenate comprises acetic acid, and wherein presence of the acetate in the extraction tower increases efficiency of separation of water from the remaining oxygenate in the extraction by the presence of acetate increasing preference of equilibrium of the acetic acid in the water as acetic acid instead of as an acetate ion.

\* \* \* \* \*